US008689651B1

(12) United States Patent
Geach

(10) Patent No.: US 8,689,651 B1
(45) Date of Patent: Apr. 8, 2014

(54) LIQUID SAMPLE TESTING APPARATUS

(71) Applicant: CINRG Systems Inc., Burlington (CA)

(72) Inventor: Alistair Geach, Burlington (CA)

(73) Assignee: Cinrg Systems Inc., Burlington, Ontario, (CA)

( * ) Notice: Subject to any disclaimer, the term of this patent is extended or adjusted under 35 U.S.C. 154(b) by 0 days.

(21) Appl. No.: 13/833,373

(22) Filed: Mar. 15, 2013

(30) Foreign Application Priority Data

Sep. 27, 2012 (CA) ...................................... 2791003

(51) Int. Cl.
*B01L 3/00* (2006.01)
*G01N 37/00* (2006.01)

(52) U.S. Cl.
USPC ........................................................ 73/864.91

(58) Field of Classification Search
USPC ........................................ 73/864.91; 206/443
See application file for complete search history.

(56) References Cited

U.S. PATENT DOCUMENTS

| 5,172,004 | A | | 12/1992 | Furuya |
| 5,426,501 | A | | 6/1995 | Hokanson et al. |
| 5,456,360 | A | * | 10/1995 | Griffin .......................... 206/443 |
| 6,927,365 | B2 | * | 8/2005 | Li .................................. 219/432 |
| 7,587,952 | B2 | * | 9/2009 | Dale et al. ................... 73/864.01 |
| 8,262,993 | B2 | * | 9/2012 | Wiederin et al. ................. 422/63 |
| 2002/0108917 | A1 | * | 8/2002 | Maruyama ....................... 211/74 |
| 2009/0155127 | A1 | * | 6/2009 | Kopoian ....................... 422/102 |

* cited by examiner

*Primary Examiner* — Hezron E Williams
*Assistant Examiner* — David Z Huang
(74) *Attorney, Agent, or Firm* — Patrick J. Hofbauer

(57) ABSTRACT

The apparatus includes a levelling mechanism having an upwardly directed reference surface adjustably mounted on a frame for supporting the base of liquid sample containers in substantially level orientation. The apparatus further includes a container positioning member having a horizontally extending main body formed with a plurality of substantially vertical container-receiving sockets. These sockets are each open at their bottom ends, so as to allow the bases of liquid sample containers to project therethrough while held within the sockets adjacent their top rims. In this manner, when the container positioning member is placed down upon the levelling mechanism, the bases of the sample containers come to rest in contact with the reference surface. Such action levels the containers to facilitate accurate automated volume measurements of liquid samples within the containers to be taken, which accuracy, in turn, increases the accuracy of automated particle counts subsequently made with the liquid samples.

20 Claims, 12 Drawing Sheets

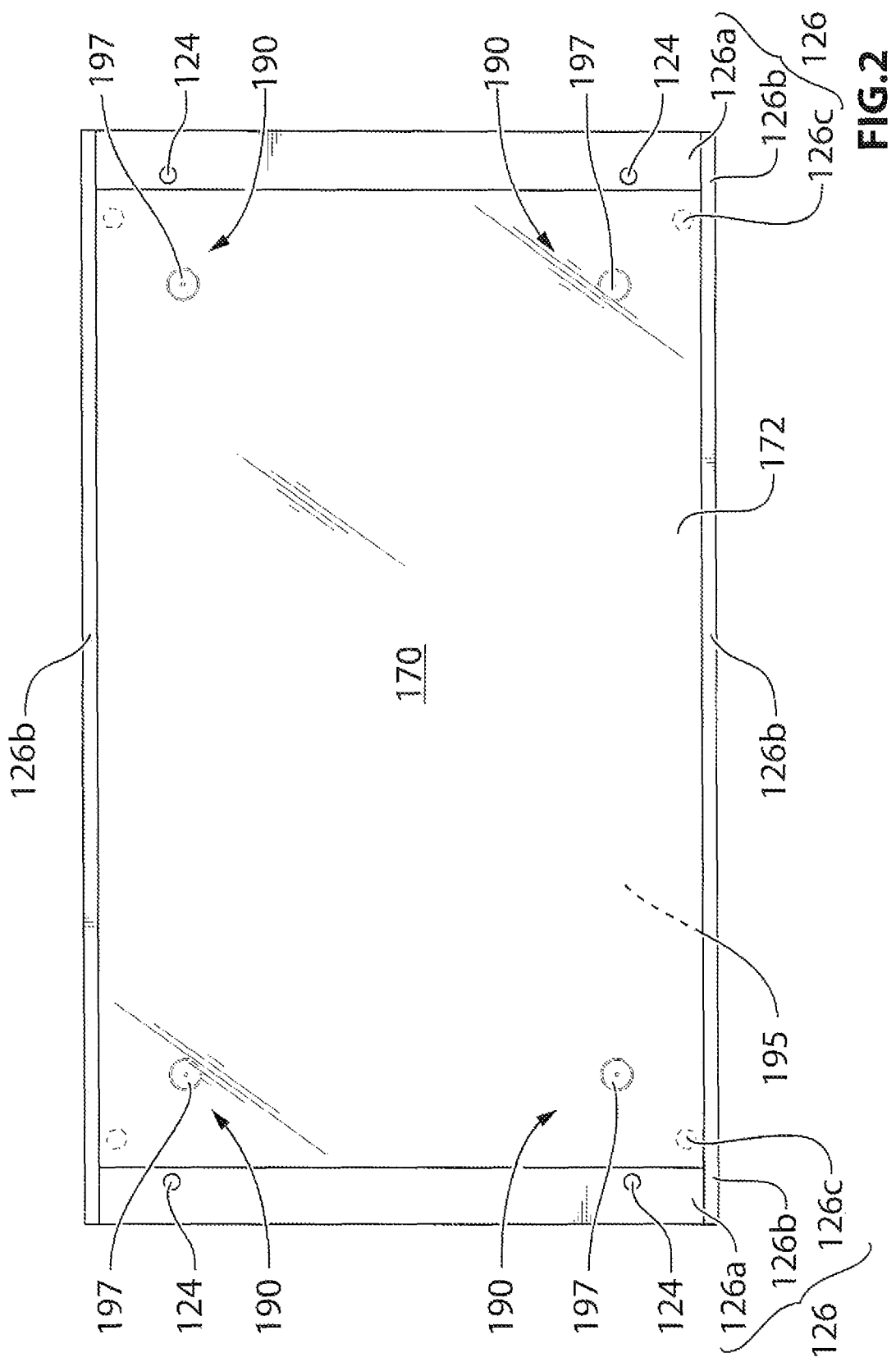

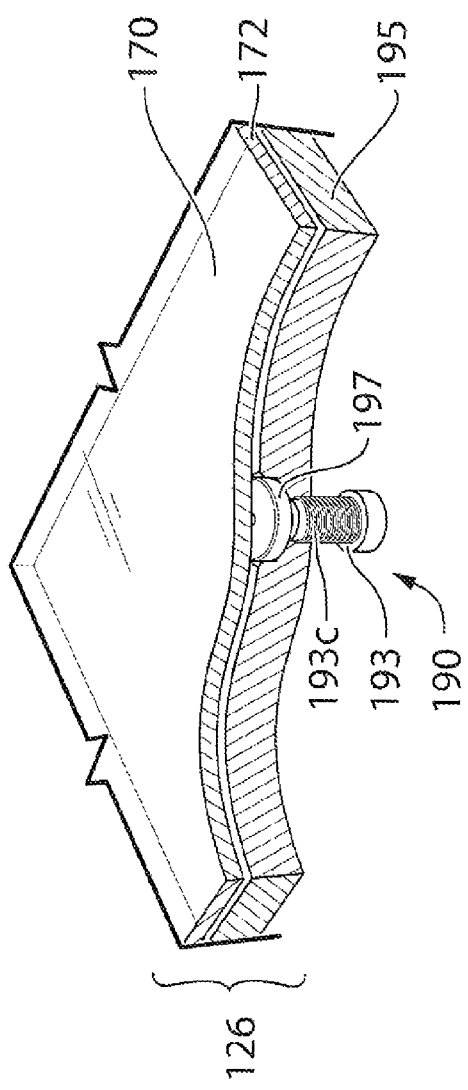
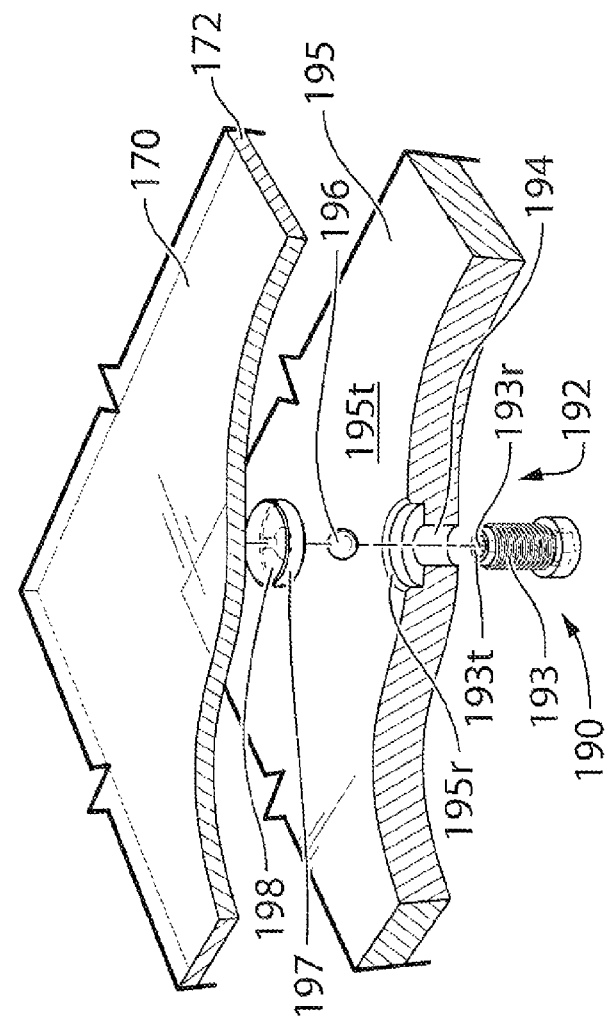
FIG.3A
FIG.3B

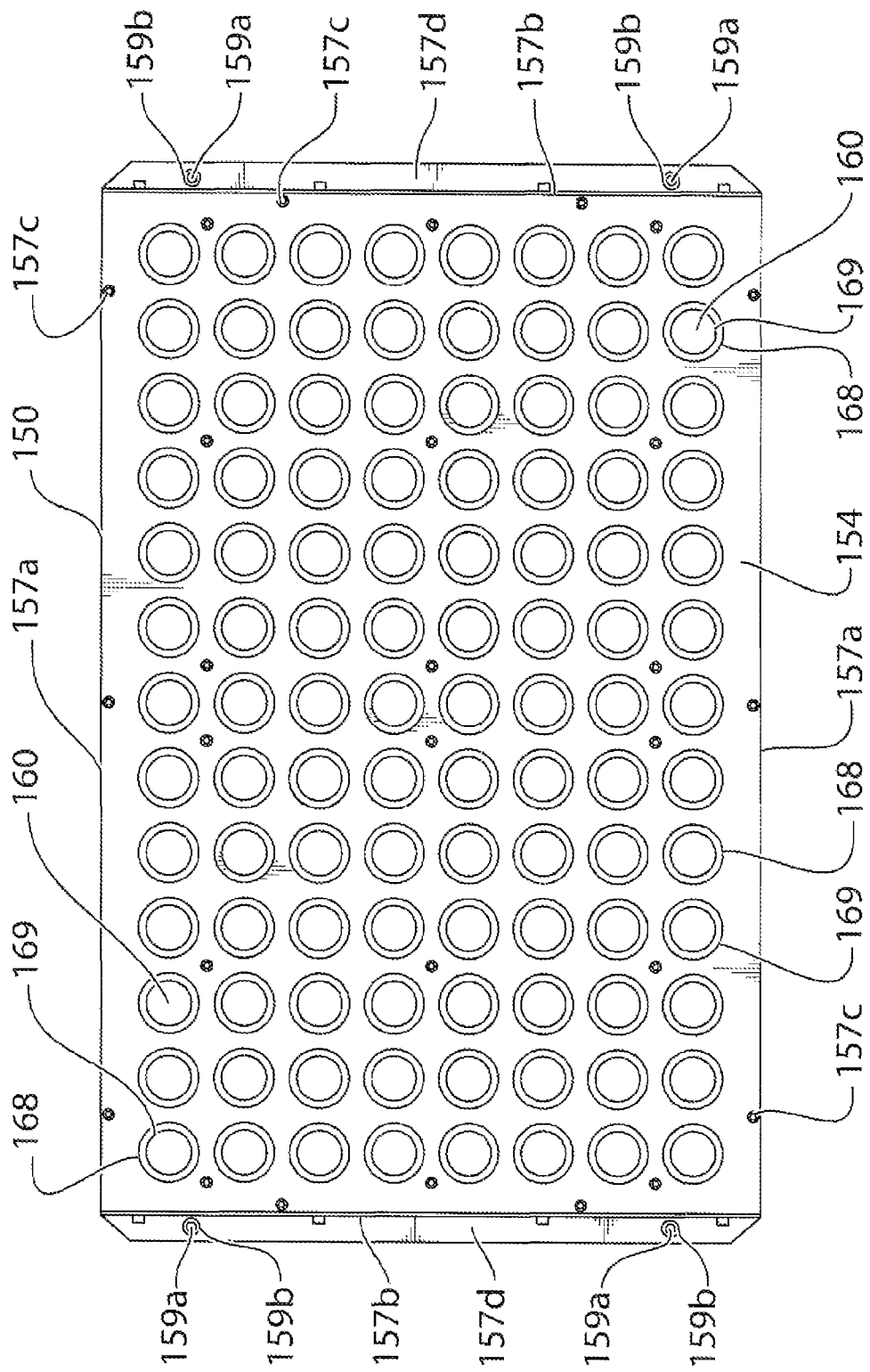

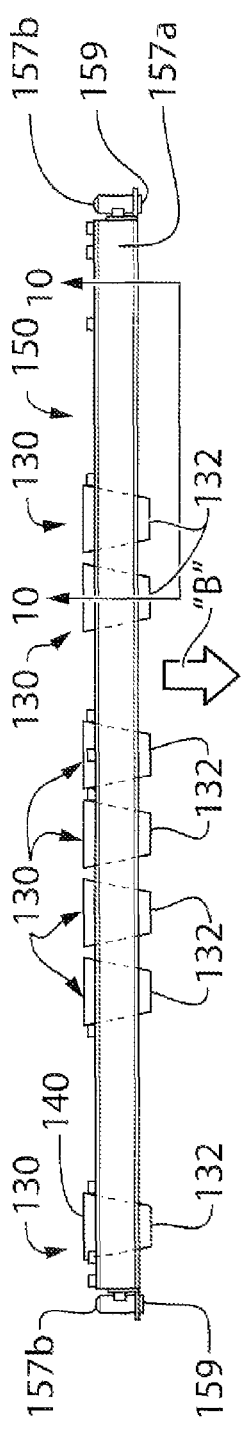
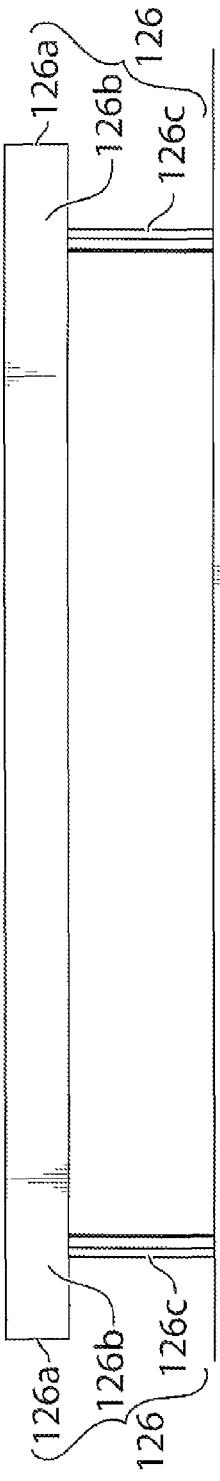
FIG.8
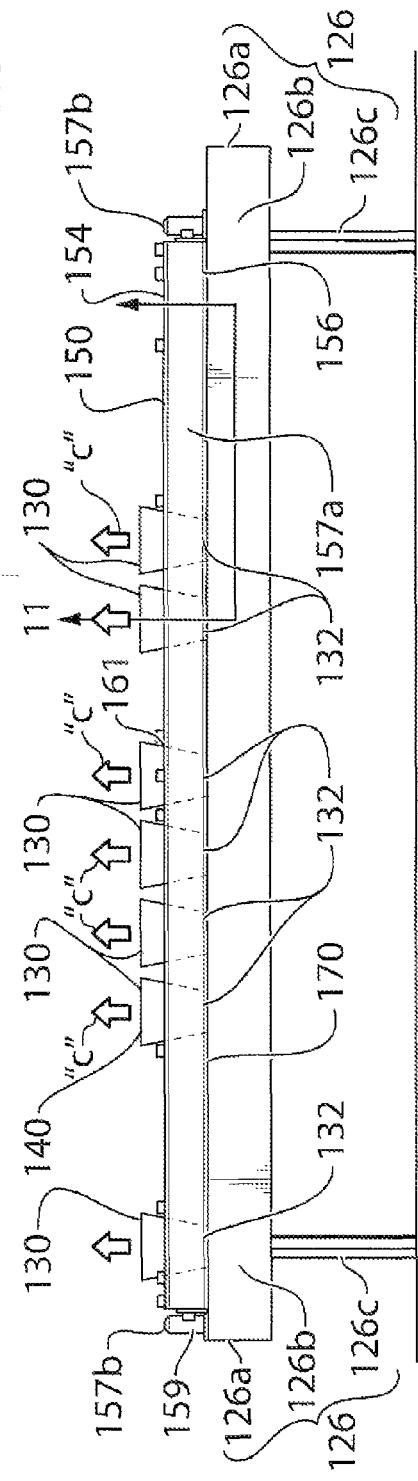
FIG.9

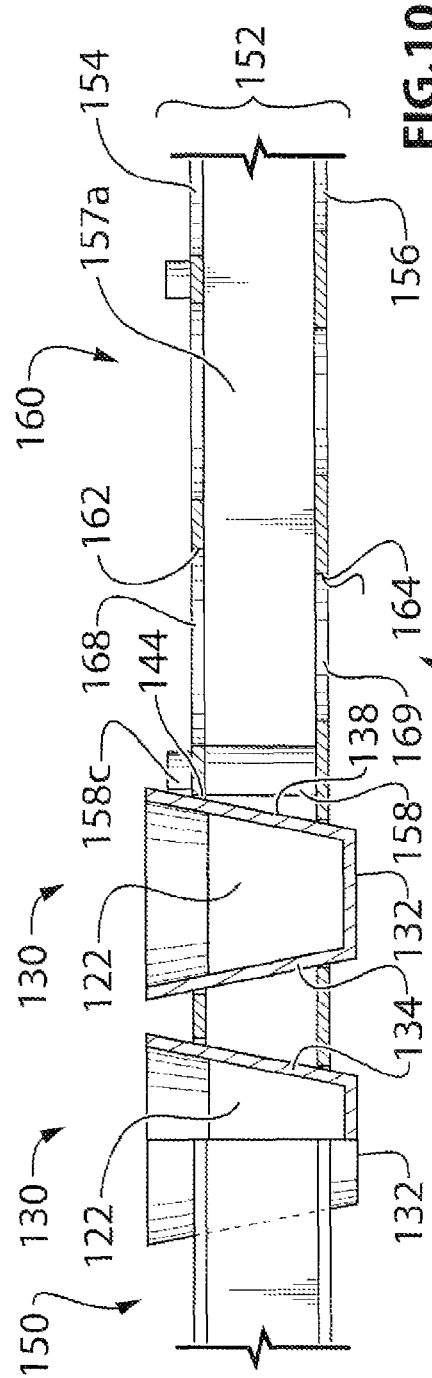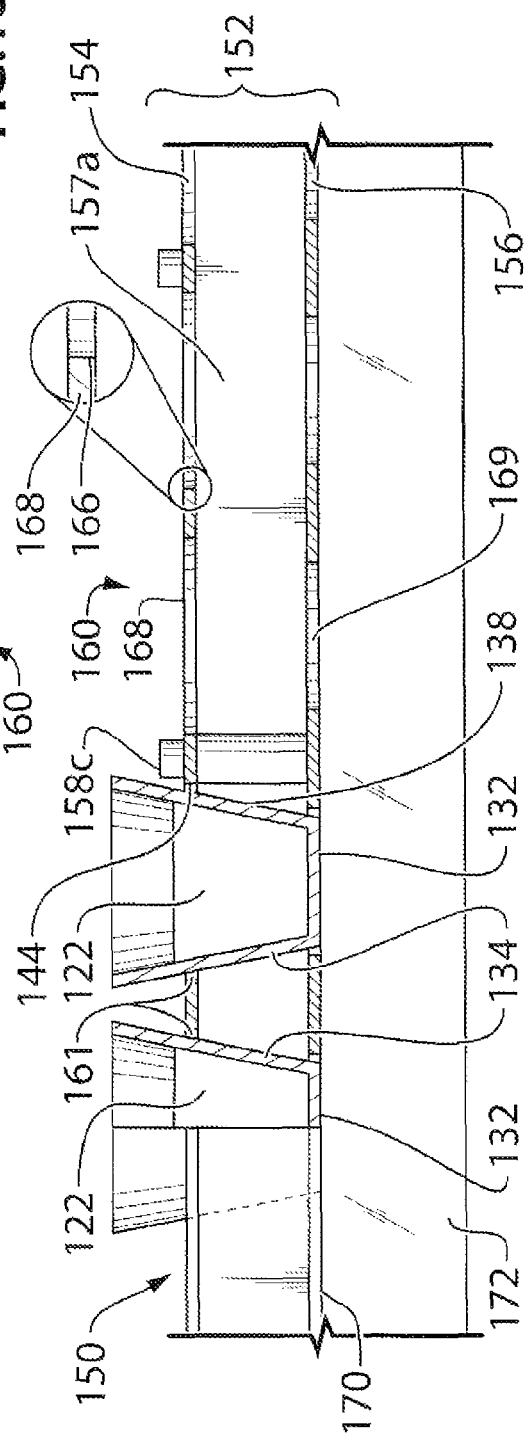

LIQUID SAMPLE TESTING APPARATUS

FIELD OF THE INVENTION

The present invention relates generally to apparatus to be used with automated particle counters for accurately determining particle counts of liquid samples contained within a plurality of uniform sample containers, using a methodology set forth in a test standard wherein diluent is added to achieve the target volume of liquid for the particle count test, and more particularly to apparatus wherein dilution ratios are calculated accurately to thereby correct particle count data for the effects of sample dilution in order to produce an accurate result for the liquid sample being tested.

BACKGROUND OF THE INVENTION

It is common to quantitatively measure the size and concentration of particulate contaminates in liquids, such as new and used oils, in order to determine various characteristics of the liquids. In samples of used oil, for instance, there are both "hard particles" that are targeted for measurement in terms of size and concentration, and similarly-sized "soft particles" that inhibit the accurate measurement of the hard particles. The presence of soft particles in a liquid sample is known to significantly elevate particle counts to the point where their presence normally invalidates the data. With the use of a suitable diluent with oil samples, these interferences can be made insignificant, or eliminated entirely.

Hard particles in oil include without limitation, dirt and metal fragments, which have a serious impact on the life of equipment by accelerating wear and erosion. Such hard particles originate from a variety of sources, including generation from within an operating fluid system, ingress into the operating fluid system, or contamination that may occur during the storage and handling of new oils. Typically, "soft particles" include certain additives or additive by-products that are semi-insoluble or insoluble in oil, and other similar materials that are not known to directly increase wear and erosion within an operating system, such as, for example, air bubbles and water bubbles.

The measurement of such contaminants is particularly important in order to identify the potential problems with samples of new or used oils, to determine the characteristics of various types of new or used oils, and also to determine whether engines and/or machinery are introducing metal particles into used oil. More particularly, particle count results can be used to aid in assessing the capability of the filtration system responsible for cleaning oil or other fluid, determining if off-line recirculating filtration is needed to clean up the fluid system, or aiding in the decision of whether or not a fluid change is required. An abnormal particle count may trigger concerns of these possibilities, which can be confirmed by additional testing.

Fundamentally, in order to permit the calculation of useful and relevant data related to particles found in fluids, such as oil, the quantity of various sizes of contaminants needs to be determined. It is well known that in order to be useful, such measurement requires quantitative guidelines in order to meaningfully present the results. Accordingly, various standards are used for testing and reporting fluid cleanliness. Two such standards include the SAE Aerospace Standard (AS) and the ISO Code System. It has been found useful to group particle sizes into coded ranges in order to permit ready handling and manipulation of the data. The following table illustrates one such standard of measurement as per the SAE Aerospace Standard (AS) system, with the codes for each range given in the left-most column.

| Cleanliness Classes for Differential Particle Counts (particles/100 ml) | | | | | |
|---|---|---|---|---|---|
| Size Code | 6 μm (c) to 14 μm (c) | 14 μm (c) to 21 μm (c) | 21 μm (c) to 38 μm (c) | 38 μm (c) to 70 μm (c) | >70 μm (c) |
| 00 | 126 | 22 | 4 | 1 | 0 |
| 0 | 250 | 44 | 8 | 2 | 0 |
| 1 | 500 | 89 | 16 | 3 | 1 |
| 2 | 1000 | 178 | 32 | 6 | 1 |
| 3 | 2000 | 356 | 63 | 11 | 2 |
| 4 | 4000 | 712 | 126 | 22 | 4 |
| 5 | 8000 | 1425 | 253 | 45 | 8 |
| 6 | 16000 | 2850 | 506 | 90 | 16 |
| 7 | 32000 | 5700 | 1012 | 180 | 32 |
| 8 | 64000 | 11400 | 2025 | 360 | 64 |
| 9 | 128000 | 22800 | 4050 | 720 | 128 |
| 10 | 256000 | 45600 | 8100 | 1440 | 256 |
| 11 | 512000 | 91200 | 16200 | 2880 | 512 |
| 12 | 1024000 | 182400 | 32400 | 5760 | 1024 |

It is well known to use automated optical particle counters to quantitatively measure the size and concentration of particulate contaminants in samples of fluids, such as new and used oil. Commonly, such particle counters are liquid optical particle counters that perform analysis based on the light extinction principle. Liquid optical particle counters are capable of recording the size and number of particles as they pass across a detector, and such equipment typically includes a sampling apparatus that automatically delivers a pre-determined volume of specimen at a controlled flow rate to the sensing zone of the analyzer. Examples of prior art particle counters are taught in, amongst others, U.S. Pat. No. 5,426,501 (Hokanson et al.) issued Jun. 20, 1995, and U.S. Pat. No. 5,172,004 (Furuya) issued Dec. 15, 1992. Indeed, tests performed by automated particle counters are considered by many to be the single most important test for oil analysis.

There are various well-known problems associated with the use of automatic optical particle counters to test samples of liquid, especially samples of oil. One of the two most fundamental problems is that of particle co-incidence. Particle co-incidence occurs when more than one particle is present in the measuring cell of the sensor at the same time and a "large" particle is falsely detected rather than two (or more) smaller ones. It is well known that particle co-incidence causes inaccurate counting Of the "hard particles" due to the presence of other type of particles, such as the "soft particles" in the liquid sample. Soft particles cause false high counts of particles in their size category, thus yielding false counts and an over-estimation of contamination levels across all sizes.

Particle co-incidence can also occur due to the existence of air bubbles in the oil, thereby causing false positive readings. Bubbles can be caused by mixing or agitating the sample, which may be necessary as part of the test procedure. Further, suspended or free water in the oil will generally be counted as particles.

Another fundamental problem associated with the use of automatic optical particle counters to test samples of liquid is that of the proper flow of high viscosity liquid samples. The forces required in order to develop the necessary pressure to rapidly achieve the required sample liquid flow rate become quite significant, and even prohibitive. It is almost impossible to properly and accurately test high viscosity liquid samples in an automatic optical particle counter without sample dilution using a suitable diluent.

The above stated problems associated with processing samples in the higher viscosity ranges, namely particle co-incidence and problems with high viscosity liquid samples are the main reasons that automated particle counters have enjoyed limited success to date.

In spite of the two above stated fundamental problems associated with the use of automatic optical particle counters to test samples of liquid, the vast majority of particle counts are still carried out on undiluted samples where the oil to be tested is sampled directly from a sample bottle without dilution. In such cases, a mechanically controlled syringe is typically used to draw up a measured volume of the liquid sample and inject it directly into the inlet port of the optical sensor of the particle counter. Alternatively, a sampling tube connected to the optical sensor inlet is lowered into the sample bottle. Pressure is used to force the sample through the optical sensor of the counter. Samples are typically processed one by one (i.e., not in a batch process), with the optical sensor cell and feeding tubes being cleaned with solvent between tested samples.

Where dilution of the liquid sample be tested is desired, it is common in the prior art to manually measure known quantities of sample liquid and of a suitable diluent for introduction into a sample container prior to testing. More specifically, a laboratory pipette is often used to manually draw a quantity of liquid from each sample bottle, as measured against volume markings on the pipette, and to inject this drawn quantity of sample liquid from the pipette into a sample container. This process may be repeated by pipette for adding a measured volume of a suitable diluent to the sample container. The two volumes are then summed for purposes of use in any subsequent calculations required to convert raw particle counts taken from a sample into standardized volumetric particle counts.

Although manual pipetting is quite accurate, it has a number of significant drawbacks associated with it, particularly where carried out repetitively for a high number of liquid samples to be subsequently presented for testing by an automated optical particle counter. These problems include, without limitation: i) pipetting is labour intensive (i.e., time consuming) for the person carrying out the procedure; ii) pipetting is tedious for the person carrying out the procedure; iii) the preparation of test samples cannot be performed outside of normal laboratory operation hours without special (and typically more expensive) arrangements being made; and, iv) persons carrying out the pipetting procedure for large numbers of test samples are susceptible to repetitive strain injuries.

In order to improve the effectiveness of optical particle counts, and to help overcame known problems, including at least those discussed above, several standardised testing protocols for optical particle counting of lubricating and hydraulic fluids have been developed and approved by ASTM International of West Conshohocken, Pa., USA. One such testing protocol, published as ASTM-D7647, is entitled "Test Method for Automatic Particle Counting of Lubricating and Hydraulic Fluids Using Dilution Techniques to Eliminate the Contribution of Water and Interfering Soft Particles by Light Extinction". ASTM-D7647 prescribes a standardized testing methodology that requires the use of a diluent to dilute the original samples to specified ratios of oil to diluent, prior to optical particle counting readings taking place. It has been found that the ASTM-D7647 test protocol notably addresses the particle count inaccuracy issues caused by particle coincidence and soft particles (as discussed above), especially where high viscosity liquids are being tested. Accordingly, the erroneous contribution of soft particles to the particle size cumulative count is substantially negated by the ASTM-D7647 methodology. The quality of particle count data is significantly improved on many samples as the effects of known interference are removed. The present invention discloses and claims, in its simplest terms, a sample presentation tray that has two main components which interact with one another and the sample containers containing liquid samples to provide for batch testing of the liquid samples according to ASTM-D7647 in a more accurate and efficient manner than has been possible with prior art sample handling apparatus.

In spite of the fact that ASTM-D7647 test protocol provides significantly more accurate automated optical particle counts than earlier testing methods, it has not gained widespread commercial acceptance. This lack of widespread commercial acceptance is thought in large part to stem from the fact that while the injection of the test sample into the optical sensor chamber and the reading of particle counts by the optical sensor may be substantially automated, the preparation and presentation of the test samples, including the addition of the aforesaid diluent, has not been significantly automated to date, and remains extremely labour intensive. In other words, the testing of oil samples using the ASTM-D7647 protocol is presently known to be used only with manual sample presentation procedures, which include pipetting, as aforesaid. As such, while ASTM-D7467 is able to obtain improved particle count results over earlier testing methodologies which do not involve the addition of a diluent to the original sample volume to be tested. the prior art drawbacks associated with pipetting, represent an ongoing limitation to its widespread commercial adoption, particularly in light of the fact that the number of pipetting operations per sample tested have necessarily been doubled over prior methodologies not utilizing sample dilution.

To carry out optical particle counting analysis according to the ASTM-D7647 protocol on a commercial scale, a large number of liquid samples must be prepared and presented for use by the automated testing equipment. One method of preparing samples for automated particle counting involves injecting a known quantity, or approximately a known quantity, of liquid to be tested into each of a plurality of like size sampling containers. Next, a quantity of solvent or other diluent is injected into the sample of liquid in the sampling containers in order to dilute the total volume of the sample liquid. This is particularly desirable where the original sample liquid is highly contaminated or highly viscous. In any case, it is necessary to determine with as much accuracy as possible both the volume of original sample liquid introduced into the sample container and of any diluent added thereto, if accurate particle counts are to be achieved.

Apart from manual pipetting of samples and diluent as discussed above, there is presently no known apparatus or method for reliably automating the preparation and presentation of test samples of oils and hydraulic fluids using an added diluent, in accordance with the ASTM-D7647 test protocol.

It is therefore an object of the present invention to provide an improved apparatus for presenting a plurality of samples of liquid contained in like size sample containers for testing by an automated particle counting system in compliance with the ASTM-D7647 testing protocol.

It is a further object of the present invention to provide an improved apparatus for presenting a plurality of samples of liquid contained in like size sample containers for automated testing by a particle counting system in a manner that eliminates the need for manual pipetting of the test samples or of any diluents added to such test samples before such testing.

It is a further object of the present invention to provide an apparatus for presenting a plurality of samples of liquid contained in like size sample containers for testing by a automated particle counting system, wherein presentation of such samples for automated testing is less labour-intensive than with known prior art apparatus and methods used for this purpose.

It is yet another object of the present invention to provide an apparatus for presenting a plurality of samples of liquid contained in like size sample containers for automated testing by a particle counting system, wherein the apparatus permits for much more prompt presentation of such samples for testing.

It is still an object of the present invention to provide an apparatus for presenting a plurality of samples of liquid contained in like size sample containers for automated testing by a particle counting system wherein the apparatus precludes the individual performing the presentation of samples from becoming unduly fatigued or from incurring repetitive strain injuries.

It is also an object of the present invention to provide an apparatus for presenting a plurality of samples of liquid contained in like size sample containers for automated testing by a particle counting system, wherein the apparatus permits comparable testing accuracy to prior art manual dilution methods that uses a pipette.

It is yet another object of the present invention to provide an apparatus for presenting a plurality of samples of liquid contained in like size sample containers for automated testing by a particle counting system, which apparatus permits an accurate automated determination of the volume of the sample liquid and of any diluent required to be added to said sample liquid in order to provide for automated filling of each said test container to a standard test volume prior to commencement of said automated testing.

It is yet another object of the present invention to provide an apparatus for presenting a plurality of samples of liquid contained in like size sample containers for automated testing by a particle counting system, which apparatus permits automated sampling of liquid samples, especially new and used oils, in the higher viscosity ranges.

It is yet another object of the present invention to provide an apparatus for presenting a plurality of samples of liquid contained in like size sample containers for automated testing by a particle counting system, the construction of which apparatus is simple, compact, and economical.

It is yet another object of the present invention to provide an apparatus for presenting a plurality of samples of liquid contained in like size sample containers for testing by an automated particle counting system, which apparatus saves the time and expense of manual sample presentation methods which make uses of pipetting, and which presents the liquid samples in a level, ordered array, so as to allow automated testing of the presented liquid samples without the need for additional manipulation or supervision of the samples during said automated testing, thereby permitting such testing to run outside of normal laboratory operational hours.

It is yet another object of the present invention to provide an apparatus for presenting a plurality of samples of liquid contained in like size sample containers for testing by an automated particle counting system, which apparatus maximizes the effective capacity of individual workers by freeing them from the need for manual pipetting of liquid samples.

It is yet another object of the present invention to provide an apparatus for presenting a plurality of samples of liquid contained in like size sample containers for automated testing by a particle counting system, which apparatus precludes workers from experiencing repetitive strain injuries by reason of the elimination of pipetting tasks associated with such presentation in the prior art.

It is yet another object of the present invention to provide an apparatus for presenting a plurality of samples of liquid contained in like size sample containers for automated testing by a particle counting system, which apparatus facilitates and promotes the adoption of the ASTM-D7647 test method on a more widespread commercial scale.

It is yet another object of the present invention to provide an apparatus for presenting a plurality of samples of liquid contained in like size sample containers for automated testing by a particle counting system, which apparatus permits the automation of the process of preparing and presenting test samples of liquid with and added diluent, in accordance with the ASTM-D7647 test protocol.

SUMMARY OF THE INVENTION

In accordance with one aspect of the present invention there is disclosed herein a novel apparatus for presenting samples of liquid contained in like size sample containers for automated testing by a particle counting system. The sample containers are substantially identical, preferably being cup-shaped and each having a base, a continuous sidewall having an inner wall surface, and an outer wall surface extending upwardly from the base to terminate at a top end of the container, thereby defining an upwardly facing open mouth of the sample container. An engagement portion of the outer wall surface is wider than the base of the sample container. The apparatus comprises a base member and an upwardly directed planar reference surface mounted on the base member for adjustment of its horizontal level. The apparatus further includes a container positioning member having a horizontally extending main body portion with a plurality of substantially vertically disposed container-receiving sockets formed therein, with the container-receiving sockets each being open at a top end and a bottom end, with each container-receiving socket being defined at said top end by a container-receiving rim portion. In an in-use sampling configuration of the apparatus, the container positioning member is positioned over the reference surface with the like size sample containers each positioned within a respective container-receiving socket and with their bases projecting through the bottom ends of said container-receiving sockets to be supported in weight bearing relation by the reference surface. In contrast, when the apparatus is removed from its in-use sampling configuration by removal of the container positioning member from over the reference surface, each of the like size sample containers moves downwardly from its position in the in-use sampling configuration relative to the container positioning member to be supported by the engagement portion of the outer wall surface contacting the container-receiving rim portion of the respective container-receiving socket in weight bearing relation therewith.

In accordance with yet another aspect of the present invention, the reference surface is adjustably mounted on the base member for adjustment of its horizontal level by at least three, and preferably four, gimbal mounts.

In accordance with another aspect of the present invention the reference surface is constructed from a sheet of plate glass.

Other objects, advantages, features and characteristics of the present invention, as well as methods of operation and functions of the related elements of the structure, and the combination of parts and economies of manufacture, will become more apparent upon consideration of the following detailed description and the appended claims with reference to the accompanying drawings, the latter of which is briefly described herein below.

BRIEF DESCRIPTION OF THE DRAWINGS

The novel features which are believed to be characteristic of the apparatus for presenting samples of liquid for testing by a particle counting system according to the present invention, as to its structure, organization, use and method of operation, together with further objectives and advantages thereof, will be better understood from the following drawings in which a presently preferred embodiment of the invention will now be illustrated by way of example. It is expressly understood, however, that the drawings are for the purpose of illustration and description only, and are not intended as a definition of the limits of the invention. In the accompanying drawings:

FIG. 2 is a top plan view of the base member of the apparatus of FIG. 1, with the container positioning member completely removed from view;

FIG. 3A is a cut-away perspective view of a portion of the base member of FIG. 2, showing one of the gimbal mounts there beneath;

FIG. 3B is an exploded cut-away perspective view of FIG. 3A;

FIG. 4 is a top plan view of the container positioning member of FIG. 1, with all of the like size sample containers removed therefrom;

FIG. 8 is a front elevational view of the apparatus shown in FIG. 1, with the container positioning member being removed from its in-use sampling configuration;

FIG. 9 is a front elevational view similar to FIG. 8, but with the container positioning member shown in its in-use sampling configuration;

FIG. 10 is a sectional front elevational view taken along section line 10-10 of FIG. 8;

FIG. 11 is a sectional front elevational view taken along section line 11-11 of FIG. 9;

DETAILED DESCRIPTION OF THE PREFERRED EMBODIMENT

Figure 1:
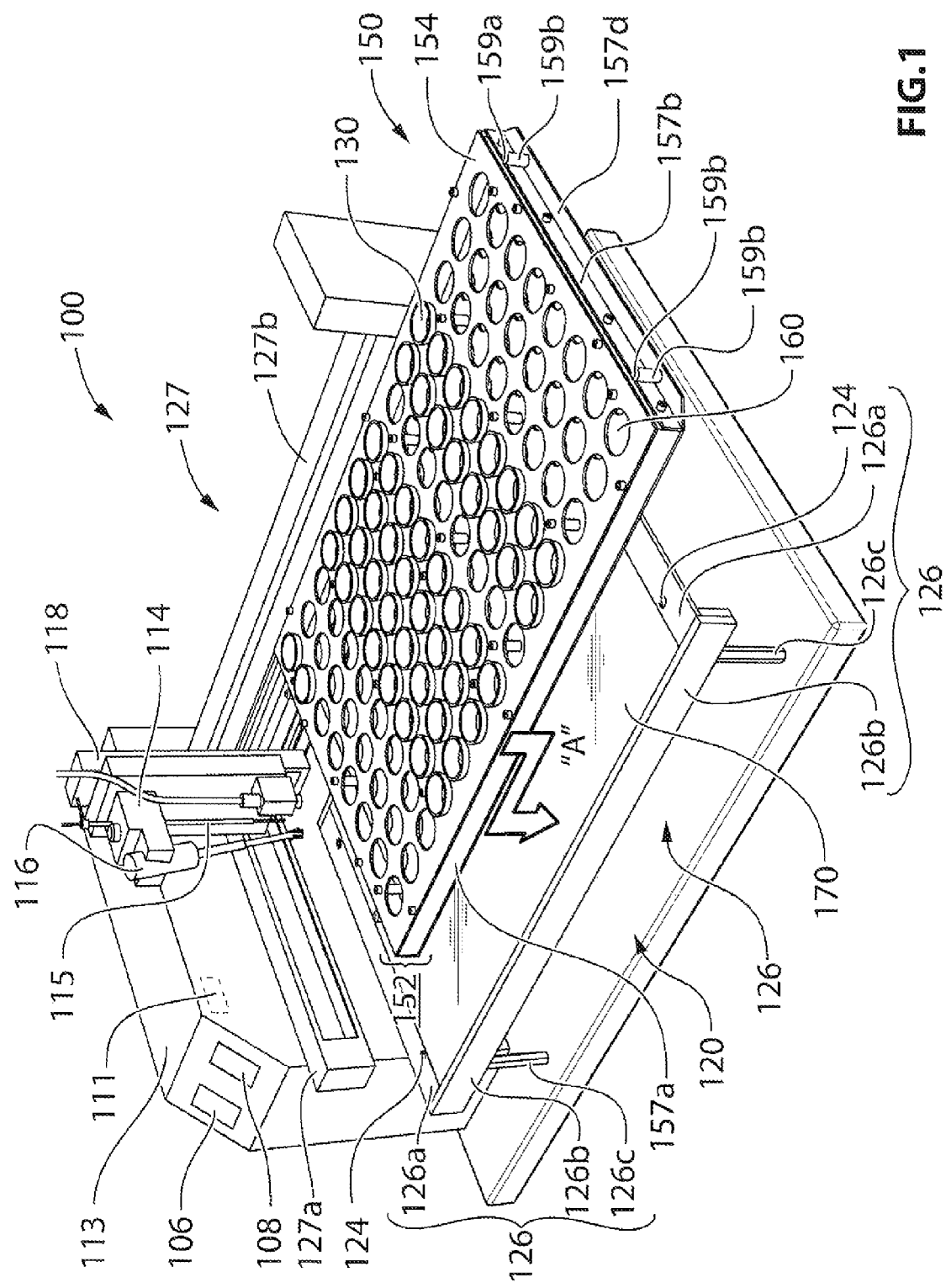
FIG. 1 is a perspective view illustrating an embodiment of an apparatus according to the invention shown in use with an automated particle counting system and with the container positioning member removed from its in-use sampling configuration.

Reference will now be made to FIGS. 1 through 15, which show an exemplary embodiment of the apparatus, as indicated by the general reference numeral 120, according to the present invention, for presenting samples of liquid for testing by an automated particle counting system, as indicated by the general reference numeral 100. Although the automated particle counting system 100 described and illustrated herein may contain subject matter that is, either alone or in combination, novel, and inventive subject matter protected by the present inventor in other patent applications filed contemporaneously herewith, it is, for the purpose of this application, not part of the invention claimed in this application. As such, it is described herein as co-operating environment only, which may be used in conjunction with the invention claimed in this application. For this reason, a general description and understanding thereof is provided in order to assist the reader in more fully understanding and appreciation the operation and utility of the presently claimed invention. In overview, the apparatus 120 claimed herein comprises, in broad terms, two main components, being a base member designated by general reference number 126, and a container positioning member 150, as will be described in more detail below. The container positioning member 150 is movable by an operator from an operative in-use sampling configuration (see FIGS. 9 and 11) wherein it rests atop the base member 126 with the base 132 of each one of a plurality of like size sample containers 130 resting on an upwardly directed reference surface 170, to a plurality of configurations (see for example FIGS. 1 and 8) wherein the container positioning member 150 is removed from such resting contact with the reference surface 170, as will be described below in considerably more detail.

Figure 13:
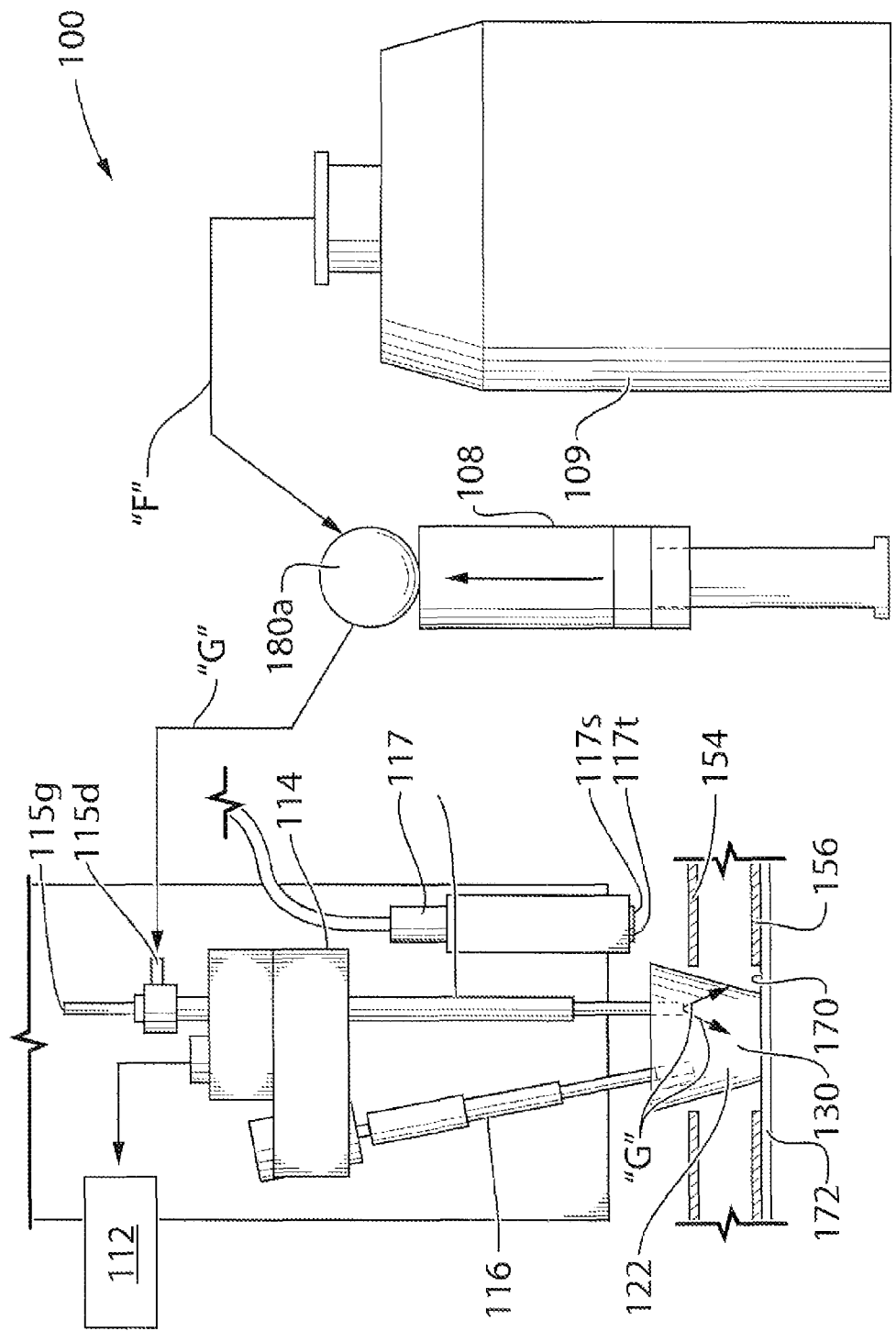
FIG. 13 is a front elevational view similar to FIG. 12, showing the sampling head with various devices mounted thereon and showing a diluent reservoir, a diluent syringe, and a delivery and uptake tube apparatus in use.
Figure 14:
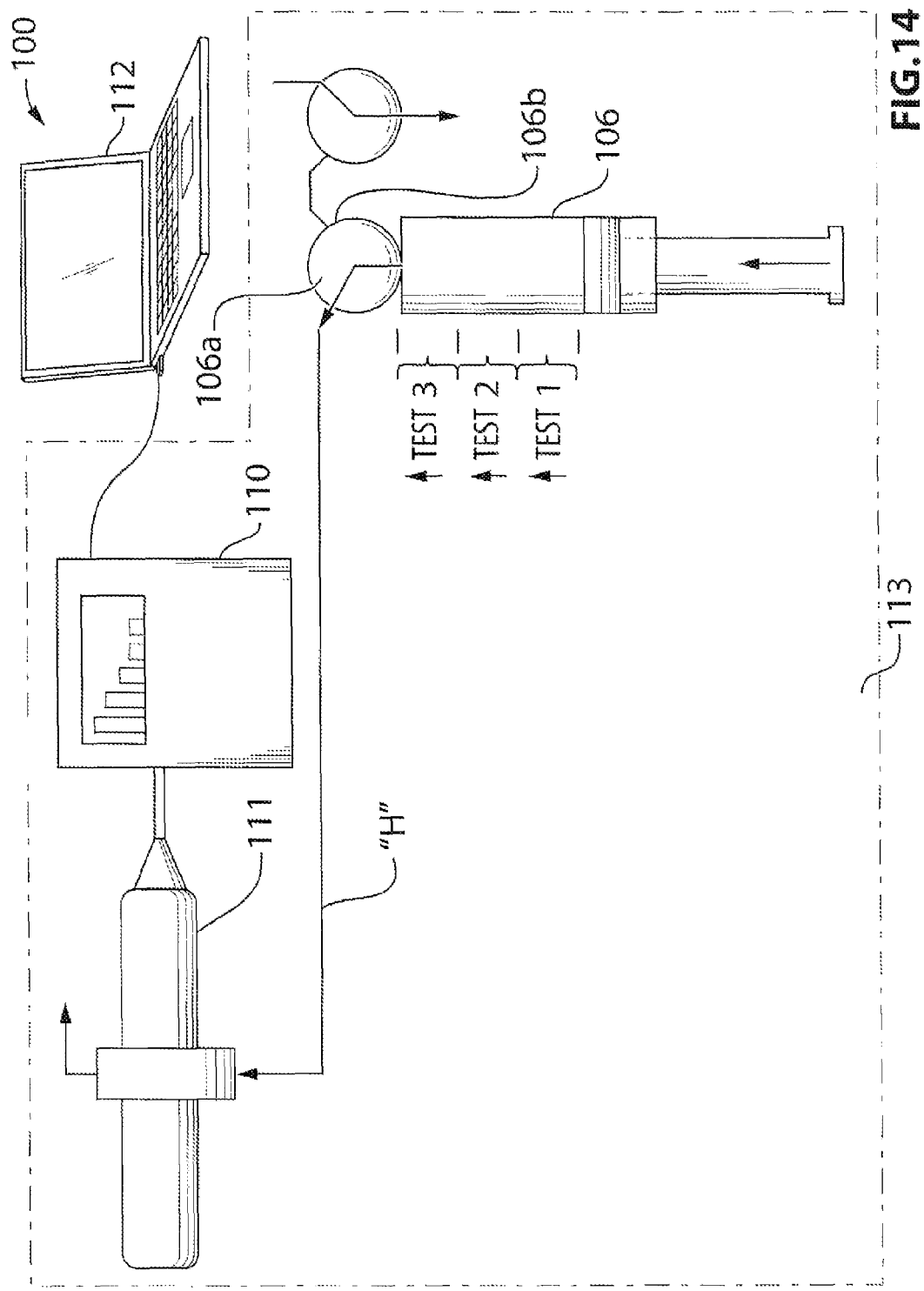
FIG. 14 is a diagrammatic sketch showing other key components of the automated particle counting system of FIG. 1 that may be used in conjunction with the apparatus of the present invention; and, FIG. 15 is an enlarged side elevational view of one of the components of FIG. 14, being a delivery and uptake tube apparatus.

As can be best seen in FIGS. 13 and 14, the particle counting system 100 used in conjunction with the apparatus 120 may comprise an automated particle counter 110, a computer 112 connected in data transfer relation to the automated particle counter 110, a sampling head 114, a delivery and uptake tube apparatus 115, a slow speed mixer 116, a small and accurate ultrasonic measuring device 117 having an ultrasonic transducer 117$t$ and an ultrasonic sensor 117$s$, a mounting mechanism 118, a sampling syringe 106, a diluent syringe 108, and a diluent reservoir 109, which may be remotely located from the other components shown. In the exemplary embodiment as illustrated, the sampling syringe 106, the diluent syringe 108, and the optical sensor 111 are preferably located in, or on, the housing 113.

The mounting mechanism 118 is used to mount a sampling head 114, a delivery and uptake tube apparatus 115, a slow speed mixer 116, and a small and accurate ultrasonic measuring device 117 in horizontally movable relation on an X-Y reference frame 127, comprised of tracks 127a and 127b, for controlled two-dimensional movement in a horizontal X-Y coordinate grid over the container positioning member 150, the sample containers 130, and the reference surface 170 when the device 120 of the invention is in its in-use sampling configuration for use with the automated particle counter 110 as described herein.

Figure 12:
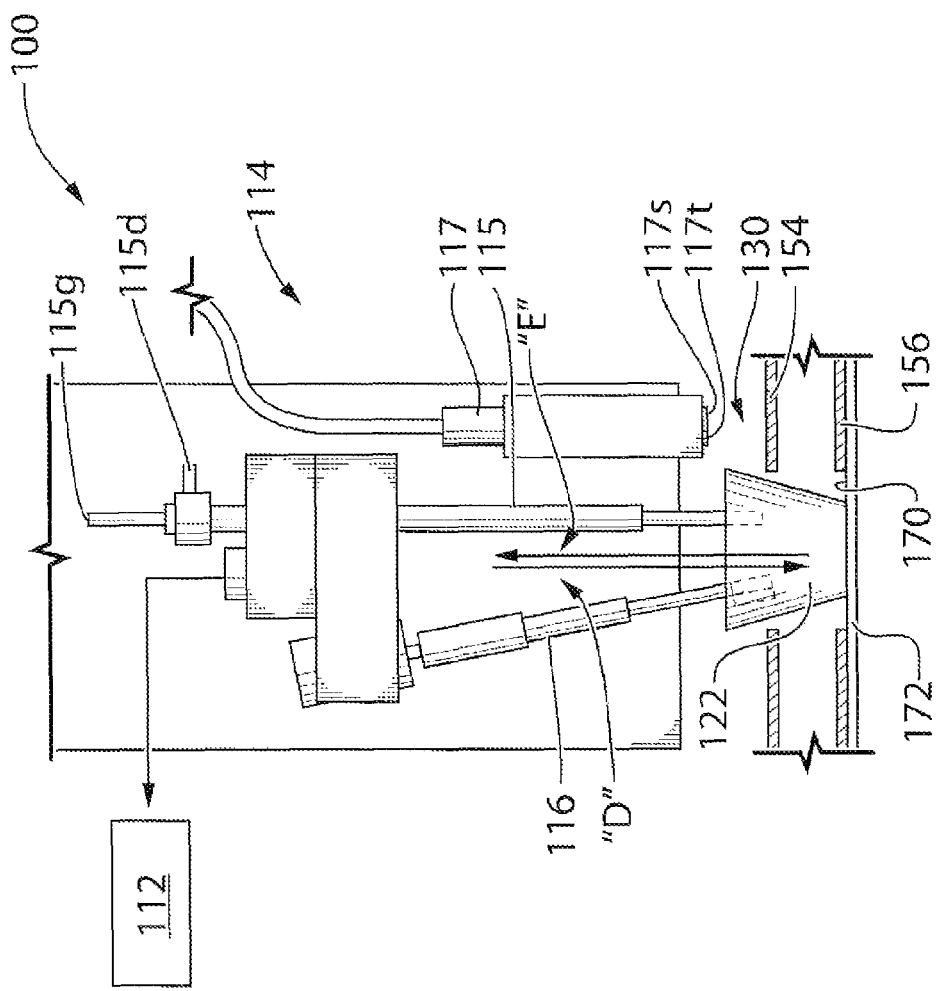
FIG. 12 is an enlarged scale front elevational view of a portion of the automated particle counting system illustrated in FIG. 1, shown in use in conjunction with the apparatus of the present invention, the illustrated portion including a sampling head with various devices mounted thereon, including an ultrasonic measuring device.
Figure 15:
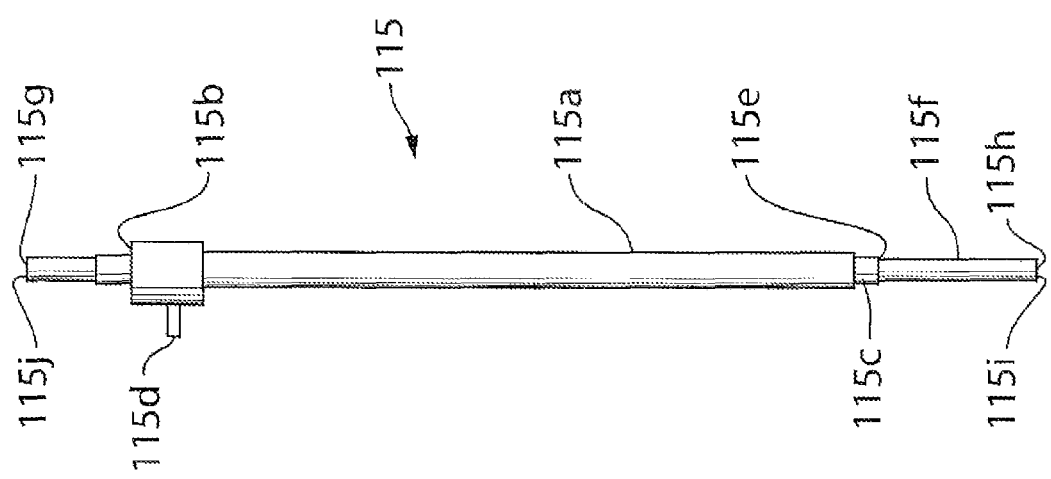

The delivery and uptake tube apparatus 115, which is shown in FIGS. 12 and 13, and in enlarged format in FIG. 15, comprises an outer diluent tube 115a and an inner delivery tube 115f. The outer diluent tube 115a has a top end 115b and a bottom end 115c, with an inlet 115d disposed adjacent the top end 115b and an outlet 115e comprising a plurality of jets disposed adjacent the bottom end 115c. The inlet 115d is connected in fluid communication to the diluent syringe 108. The inner delivery tube 115f has a top end 115g and a bottom end 115h, with an inlet 115i disposed adjacent the bottom end 115h and an outlet 115j disposed adjacent the top end 115g. The outlet 115d is connected in fluid communication to the optical sensor 111 of the computer 112.

This double tube arrangement separates the sample and diluent supply streams. Diluent enters the outer diluent tube 115a near the top end 115b through the inlet 115d the flows from the outer diluent tube 115a over the inner delivery tube 115f, and egresses the outer diluent tube 115a through the outlet 115e at the bottom end 115c. Sample liquid enters the inner delivery tube 115f through the inlet 115i disposed at the bottom end 115h and egresses the inner delivery tube 115f through the outlet 115j disposed adjacent the top end 115g. The inner delivery tube 115b is slidably mounted within the outer diluent tube 115a. The outer diluent tube 115a acts as a guide and eliminates the need for a conventional two-tube junction.

In conjunction with the device 120 of the present invention, an automated particle counter 110 performs automated particle counts of liquid samples 122 presented by the device 120 and contained within the plurality of substantially uniform sample containers 130. As an integral part of the process, the volume of liquid in each sample container must be determined with considerable accuracy in order to achieve an accurate particle count for the liquid sample 122 being tested. It is critical in this regard that all the sample containers 130 sit on a common flat and level reference surface to ensure consistency when sample height measurements are taken by the ultrasonic measuring device 117. It has been found that the device 120 of the present invention produces a potential sample volume error of leas than 2%, which is well within acceptable tolerances for the ASTM-D7674 test method, which tolerance level is unknown in the prior art so far as automated liquid sample dilution and presentation systems are concerned.

In order to accurately perform volumetric calculations of sample liquid in the sample containers received and retained by the cup positioning member 150, the ultrasonic measuring device 117 with its ultrasonic transducer 117t and its ultrasonic sensor 117s is used. the ultrasonic measuring device 117 uses very small sensor (VSS) technology, and is used to accurately measure the height of liquids in the like size sample containers 130. The ultrasonic measuring device 117 is preferably incorporated into a plastic mounting member 119 mounted on the bottom end 118a of the mounting mechanism 118 that carries the moveable sampling head 114 of the automated particle counting system 100. Data can be obtained from the ultrasonic sensor and is used by the computer 112 to quickly and accurately calculate the volume of sample liquid, such as used oil, to be tested in each like size sample container 130 immediately before proceeding with dilution of each sample.

Generally speaking, for each like size sample container 130 containing a sample liquid 122, the transducer 117t and the sensor 117s of the ultrasonic measuring device 117 are moved to a fixed X-Y coordinate position directly above the sample container 130. An ultrasonic wave is emitted from the ultrasonic transducer 117t, and reflected from the surface of the liquid 122 in the sample container 130. The reflected ultrasonic wave is received back at the sensor 117s and the time difference between emission and reflection is measured, and is used to determine the height of the top surface of the liquid 122. Once the height of the top surface of the liquid 122 in the like size sample container 130 is established in this manner, the volume of liquid 122 in the sample container 130 can be determined from the geometry of the sample container 130. If desired, the volume of diluent that will be needed to dilute the sample liquid 122 to a final volume for testing, can then be calculated by the computer 112 and automatically added to the liquid sample in the sampler container 130. It has been found that a suitable diluent is one such as a solvent comprising, for example, 75% toluene and 25% Propan-2-ol.

Figure 5:
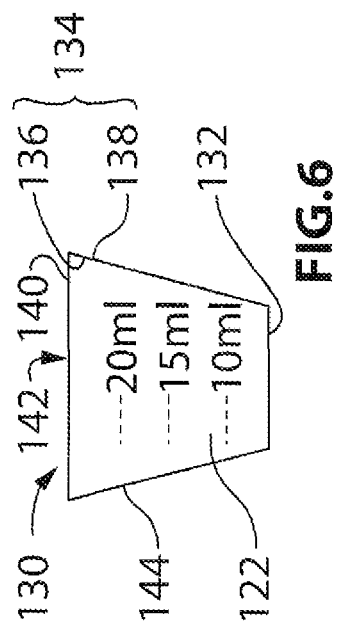
FIG. 5 is an enlarged side elevational view of an empty sample container.
Figure 6:
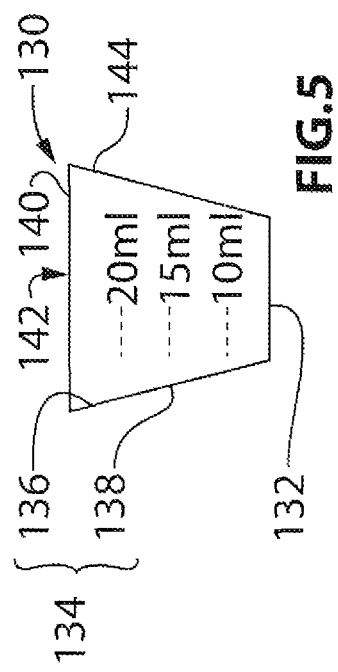
FIG. 6 is an enlarged side elevational view of the sample container of FIG. 5, but with an aliquot of sample liquid therein.

Reference will now be made to FIGS. 5 through 11, which figures show the like size sample containers 130 being prepared and presented for batch testing according to the present invention. FIG. 5 shows an empty like size sample container 130 about to have an aliquot of sample liquid 122 poured into it, and sequentially FIG. 6 shows a sample container 130 having about seventeen (17) milliliters of sample liquid having been manually poured by a laboratory technician into it, after the sample liquid has been sufficiently mixed to evenly distribute any contaminants. FIGS. 7 through 11 show a plurality of like size sample containers 130 retained by the container positioning member 150 being manipulated into place on the reference surface 170 of the apparatus 120. While an aliquot of sample liquid 122 having a volume of about seventeen (17) milliliters has been manually poured into each of the like size sample containers 130 by a laboratory technician without pipetting, the exact volume is unimportant, so long as the volume is below the target volume of thirty (30) milliliters.

The main operational advantage of the present invention, namely the apparatus 120, is that it allows approximate volumes of oil samples that are to be tested to be manually poured by laboratory personnel directly into like size sample containers 130. This method of directly pouring the oil samples into the like size sample containers 130 is quick, simple, and easy. Most importantly, it also eliminates the use of a pipette for handling of the liquid samples and of the diluent, thereby ameliorating, or even entirely eliminating, the known disadvantages associated with pipetting, as mentioned previously, namely a high labour content and associated costs, lack of availability of labour during off hours, slowness of the process, and repetitive strain injuries to pipetting personnel.

Figure 7:
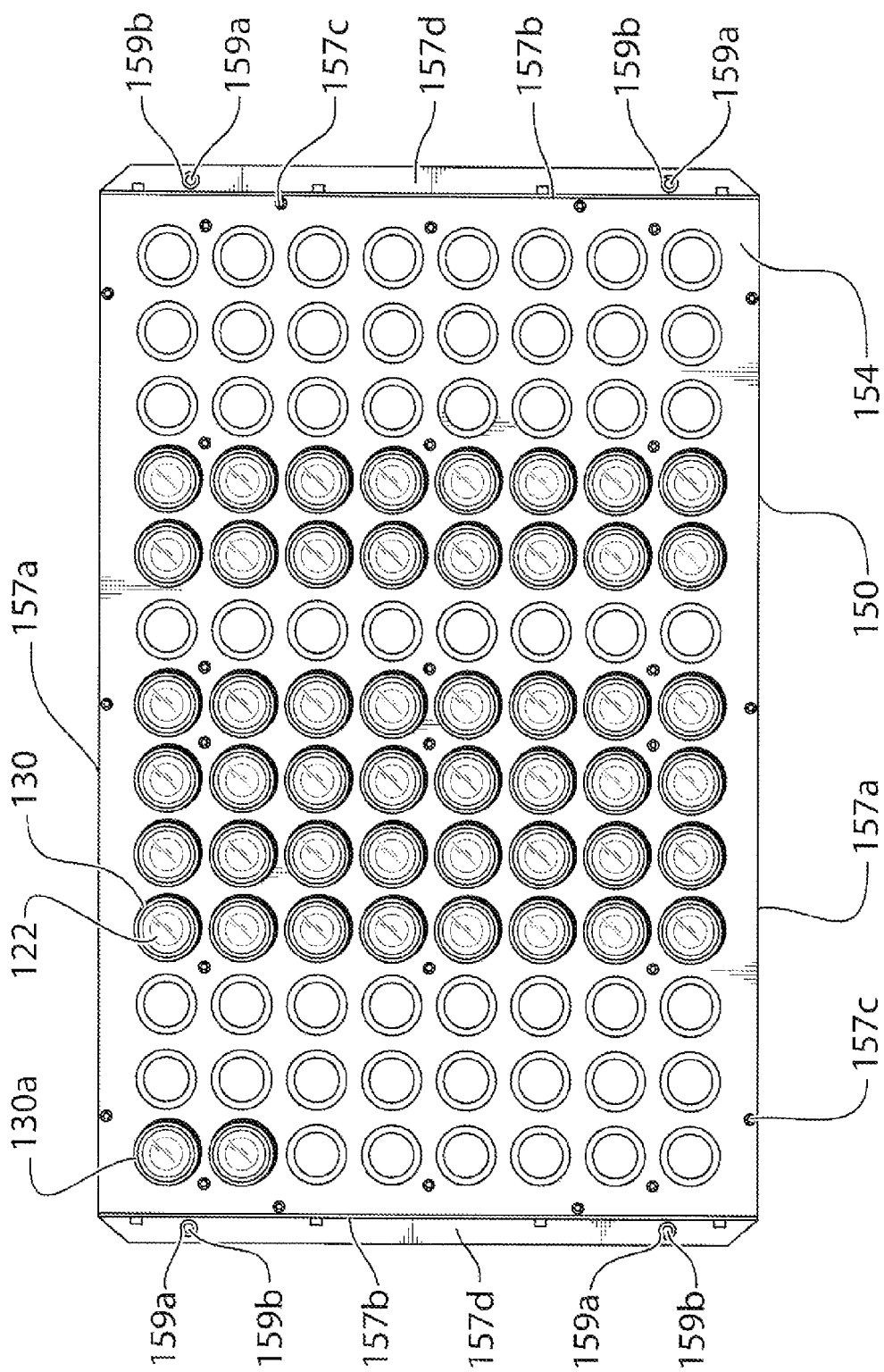
FIG. 7 is a top plan view similar to FIG. 4, but with the like size sample containers of FIG. 1 in place therein.

FIG. 7 is a top plan view of the container positioning member 150 and a plurality of like size sample containers 130, and shows that the first two positions may contain empty like size sample containers 130, as they may be used for storing diluent and for system cleanliness verifications. Diluent from the reservoir 109 (see FIG. 13) is delivered to the sample container 130a in position number "one" (i.e., Column 1, Row 1 in FIG. 7) and used to flush the delivery tubing and the optical sensor 111 of the automatic particle counter 110 prior to diluent verification. Further, diluent from the reservoir 109 is dispensed to the sample container 130b in position number "two", (i.e., Column 1, Row 2 in FIG. 7) for example, and twenty-five (25) milliliters of this diluent aspirated to the sampling syringe 106.

In order to determine the volume of sample liquid 122 in the sample container 130 being tested, and also to determine the volume of diluent that will be needed to dilute the sample to a target volume for testing of, for example, thirty (30) milliliters, data from the ultrasonic height sensor 117 in the sampling head 114 is transferred to the computer 112. A batch file containing the position of the cup positioning member 150 and other information related to the sample liquid 122 in the like size sample containers 130 is stored on the computer 112 controlling the automated particle counter 110.

Depending on the viscosity and expected cleanliness of the sample liquid, each sample is preferably diluted before testing by means of the addition of a suitable diluent (solvent) added to each sample container 130 such that the volume added is preferably between three (3) milliliters (1:10 dilution) and fifteen (15) milliliters (1:1 dilution), assuming a thirty (30) milliliter sample container is utilized. The diluted samples must then be thoroughly agitated in order to fully mix the diluent and the sample liquid 122. In order to accomplish this, the sampling head. 114 moves under control of the computer 112 down into the sample container 130 and the slow speed mixer 116 is started. The required volume of diluent is then added to the sample container 130 through the diluent tube 115a to dilute the sample, as previously explained. The sample is mixed under control of the computer 112 for a specified time to dissolve the sample in the diluent and suspend the various particulates.

After the mixing period, the sampling syringe 106 is programmed to aspirate a volume of approximately six (6) milliliters from the sample container 130 through the delivery tubing 105 and into the sampling syringe 106. The sampling syringe 106 is then programmed to dispense the sample volume of six (6) milliliters to the optical sensor 111 and to eject displaced air from the syringe and to flush the sensor with about three (3) milliliters of a new sample. A further volume of approximately twenty-three (23) milliliters of sample liquid 122 is then aspirated to the sampling syringe 106. A valve 106a is switched by the computer 122 to isolate the inlet port 106b of the syringe 106. The sampling syringe 106 is further programmed to aspirate a small additional volume against the closed inlet port 106b in order to create a partial vacuum in the syringe and degas the sample liquid 122. After a specified degassing period, the sampling syringe 106 is programmed to dispense the additional volume to restore near normal pressure.

Once the sample liquid 122 has been degassed, as aforesaid, the sample analysis takes place within the optical sensor 111. After degassing, three separate tests are preferably conducted sequentially by the particle counting system 100. In each of the three tests, five (5) milliliter samples of diluted sample liquid 122 is counted. The data set is tested for ASTM D7647 validity and an average result calculated by the computer 112. All measured and calculated data is stored in a sample specific text file in the computer 112.

Reference will now be made to the figures for a more specific description of the present invention, namely the apparatus 120 for presenting samples of liquid for testing by an automated particle counting system, such as that just described.

In the embodiment illustrated, the apparatus, as indicated by the general reference numeral 120, is used for presenting the samples of liquid 122 contained in like size sample containers 130 for automated testing by an automated particle counting system, as indicated by the general reference numeral 100, and as can best be seen in FIGS. 1 and 14. The like size sample containers 130 are substantially identical to one another and are, preferably, cup-like in shape (without a handle) and may, for reasons of availability and economy, be the same as, or similar to, the well known plastic pill containers used in hospitals and the like to dispense a dosage of pills or other medicine to patients of such facilities. In any event, each container 130 has a base 132, and a continuous sidewall 134 that is preferably annular in shape so that the rotational orientation of each like size sample container 130 during use is not relevant, Preferably, but not essentially, the like size sample containers 130 are each frustum shaped. As can be best seen in FIGS. 5, 6, 8 and 9, the continuous sidewall 134 of the like size sample containers 130 each has an inner wall surface 136 and an outer wall surface 138, and extends upwardly from the base 132 to terminating at a top end 140 to thereby define an upwardly facing open mouth 142. There is also an engagement portion 144 of the outer wall surface 138 that is wider than the base 132 and closer to the mouth 142 than to the base 132. The engagement portion 144 is dimensioned for engaging the container positioning member 150, in one configuration (only) of the container positioning member 150, as will be discussed subsequently in greater detail.

More specifically, the apparatus 120 includes the container positioning member 150, which comprises a horizontally extending main body portion 152. In the preferred embodiment, as illustrated, the main body portion 152 preferably, but not essentially, comprises an upper plate 154 and an optional lower plate 156, which may be connected together in secure relation by peripheral side walls 157a and peripheral end walls 157b and by a plurality of spacers 158. The upper plate 154 and the lower plate 156 may be secured together via the peripheral side walls 157a and peripheral end walls 157b by threaded fasteners 157c. Further, the upper plate 154 and the lower plate may be secured together via the plurality of spacers 158 by threaded fasteners 158c. There are also preferably provided two horizontally outwardly projecting end flanges 157d disposed one flange at each end of the main body portion 152.

The upper plate 154 and the lower plate 156 are each preferably substantially planar and substantially parallel one to the other. For the sake of strength and rigidity, the main body portion 152 is made substantially from metal components and, preferably from aluminium-based materials, or from stainless steel-based materials. Alternatively, the container positioning member 150, and/or any of the components thereof, may be made from any other suitably rigid and robust material.

As can best be seen in FIGS. 8 and 9, the main body portion 152 of the container positioning member 150 comprises a plurality of substantially vertically disposed container-receiving sockets 160 formed in the main body portion 152. Preferably, the substantially vertically disposed container-receiving sockets 160 are arranged in a rectangular matrix pattern in order to simplify the positioning of the sampling head 114 during use of the apparatus 120. Further, the substantially vertically disposed container-receiving sockets 160 are substantially annular in plan outline, in order to help control and minimize the vertical and lateral movement of the like size sample containers 130 during use.

Each of the container-receiving sockets 160 preferably has a top end 162 and a bottom end 164, and is open at the top end 162 and the bottom end 164, in order to permit a sample container 130 to extend therethrough. Each container-receiving socket 160 is defined at the top end 162 by a container-receiving rim portion 166. In the preferred embodiment illustrated, each of the substantially vertically disposed container-receiving sockets 160 comprises an upper container-receiving aperture 168 in the upper plate 154 and a lower container-receiving aperture 169 in the lower plate 156 in axial alignment with the upper container-receiving aperture 168 (beat seen in FIGS. 10 and 11).

The container positioning member 150 further comprises a plurality of feet 159 projecting downwardly from the main body portion 152 at each of the two horizontally outwardly projecting end flanges 157c. As can be best seen in FIGS. 8 and 9, each of the feet 159 is secured in place on the bottom of the two horizontally outwardly projecting end flanges 157c by a co-operating threaded fastener 159a extending downwardly through co-operating through passages (not specifically shown) in the cylinders 159b disposed above the outwardly projecting end flanges 157c and through apertures (not specifically show) in the horizontally outwardly projecting end flanges 157c, to each threadingly engage one of the feet 159, to thereby secure the feet 159 in a fixed vertical orientation as illustrated.

A corresponding plurality of co-operating foot-locating recesses 124 (see FIGS. 1 and 2) may optionally be formed in opposed side rails 126a of the base member 126 adjacent to the reference surface 170, for receiving the feet 159 in stable indexed relation therein when the container positioning member 150 is placed over the reference surface 170 in the operative in-use configuration (see FIGS. 4, 7, 9, and 11).

The base member 126, which structure may be generally table-like, having parallel front and back rails 126b, 126b rigidly connected to opposed side rails 126a, 126a, with the space between all four rails being occupied by a horizontal base plate 195 rigidly connected to the rails. All four rails 126a, 126a, 126b, 126b preferably stand proud of the horizontal base plate 195, so as to define a cavity of quadrilateral plan outline, in which cavity the reference surface 170 may be located as shown. Ideally, but not necessarily, the reference surface 170 is mounted so as to extend upwardly from within the cavity to approximately the same height as the upper surfaces of the four rails 126a, 126a, 126b, 126b. A set of four legs 126c complete the table-like structure that is the base member 126. The components of the base member 126 are preferably constructed from the same general type of metal materials as is the container positioning member 150.

The base member 126 has a reference surface 170 mounted thereon for adjustment of its horizontal level. Preferably, the reference surface 170 is planar, and may, as shown, be constructed from a sheet of plate glass 172 which presents its upper surface as the reference surface 170. It has been determined by the inventor that a high quality precision formed sheet of plate glass provides a reference surface 170 having a height variation of less than 0.025 mm across its upper surface, which is sufficiently flat for most testing discussed herein at a reasonable cost, as compared to having a similarly dimensioned reference surface constructed from plate metal, the letter of which would typically require a costly machining operation to achieve a similar degree of levelness (i.e. flatness) across its upper surface.

The reference surface 170 may be mounted on the base member 126 for adjustment of its horizontal level as aforesaid by means of at least three gimbal mounts 190 (one of which is illustrated in detail in FIGS. 3A and 3B), atop of which gimbal mounts 190 the reference surface 170, specifically the sheet of plate glass 172, sits. In the embodiment illustrated, four gimbal mounts 190 are positioned adjacent each of the four corners of the reference surface 170 (see FIG. 2). If required, a fifth gimbal mount (not shown) may also be centrally positioned between the four gimbal mounts shown to support the underside of the reference surface 170 adjacent its middle area. This may be particularly advantageous where very large sheets of plate glass are employed.

Each of the four gimbal mounts 190 may comprise a vertically oriented threaded member 193 threadibly engaged in a co-operating threaded aperture 194 in the horizontal base plate 195 of the table frame 126. A concave recess 193r in the top end 193t of the vertically oriented threaded member 193 receives a ball bearing 196 in weight bearing relation. The ball bearing 196 receives a disk member 197 at a downwardly facing recess 198 in weight bearing relation. The disk member 197 resides at least partially within a circular recess 195r in the top surface 195t of the horizontal base plate 195. In this manner, the sheet of plate glass 172 that presents the reference surface 170 rests in vertically adjustable supported relation on the four disk members 197. While a relatively small degree of self-levelling is built into the gimbal mounts 190 as illustrated and described, the vertically oriented threaded members 193 are each independently rotatable to thereby selectively move the four disk members 197 up and/or down, as necessary, to more fully adjust the horizontal level of the reference surface 170 until an operatively acceptable degree of horizontal level of the reference surface 170 is achieved.

In an in-use sampling configuration of the apparatus 120, as can be best seen in FIGS. 10 and 11, the container positioning member 150 is positioned over the base member 126 and the reference surface 170, with the like size sample containers 130 each positioned within a respective container-receiving socket 160. More specifically, the like size sample containers 130 each project through both the upper container-receiving aperture 168 in the upper plate 154 and the lower container-receiving aperture 169 in the lower plate 156. As such, the bases 132 of each of the like size sample containers 130 project through the bottom ends 164 of the container-receiving sockets 160 at the lower container-receiving aperture 169, to thereby be supported in weight bearing relation by the reference surface 170.

It will also be noted that when the container positioning member 150 is in the in-use sampling configuration, the plurality of substantially vertically disposed container-receiving sockets 160 are positioned, shaped and dimensioned such that a gap 161 exists, as is best seen in FIG. 10, between the engagement portion 144 of the outer wall surface 138 of the like size sample containers 130 and the container-receiving rim portion 166 of the respective container-receiving socket 160. In this manner, the like size sample containers 130 have basically been temporarily released from contact with the container positioning member 150 in order to be fully supported by the reference surface 170.

Further, in the in-use sampling configuration of the apparatus 120, the container positioning member 150 is supported in weight bearing relation by the apparatus 120 adjacent the reference surface 170, by means of its feet 159 engaged in the co-operating foot-locating recesses 124 in the table frame 126 adjacent the reference surface 170.

As can be best seen in FIGS. 8 and 10, when the apparatus 120 is removed from its in-use sampling configuration by, for example, upward removal of the container positioning member 150 from positioning over the reference surface 170, each of the like size sample containers 130 moves downwardly from its position in the in-use sampling configuration, relative to the container positioning member 150, to be supported by the engagement portion 14 of the outer wall surface 138 contacting the container-receiving rim portion 166 of the respective container-receiving socket 160 in weight bearing relation therewith. The container positioning member 150 and the like size sample containers 130 retained by the container positioning member 150 with the liquid samples 122 therein can then readily be carried away from the base member 126 by a user.

Reference will now be made to FIGS. 1 and 5 through 13, which show the apparatus 120 according to the present invention in use. As can be best seen in FIGS. 5 and 6, the like size sample containers 130 are being prepared for testing as a sample batch. FIG. 5 shows an empty sample container 130 ready to have an aliquot of sample liquid 122 manually poured into it, and sequentially FIG. 6 shows a sample container 130 having about seventeen (17) millilitres of sample liquid having been poured into it, after the sample liquid has been sufficiently mixed to evenly distribute any contaminants. FIGS. 1 and 7 through 11 show a plurality of like size sample containers 130 retained by the container positioning member 150 in place on the reference surface 170. An aliquot of sample liquid 122 having a volume of about seventeen (17) millilitres has been poured into each of the like size sample containers 130. The exact volume is unimportant as long as the volume is below the target volume of thirty (30) millilitres.

As can be seen in FIGS. 8 and 10, when the container positioning member 150 is removed from the in-use sampling configuration, the partially full like size sample containers 130 are supported by the engagement portion 144 of the outer wall surface 138 contacting the container-receiving rim portion 166 of the respective container-receiving socket 160 in weight bearing relation therewith. This configuration would be realized in, for example carrying the container positioning member 150 and the like size sample containers 130 to the base member 126 and the associated particle counting system 100, or removing it therefrom after the optical particle counting testing has been completed. Arrow "A" in FIG. 1 and arrow "B" in FIG. 8 indicate movement of the container positioning member 150 and sample containers 130 contained thereby into the operative in-use configuration by being lowered into position atop the base member 126, as the feet 159 are indexingly received by the co-operating foot-locating recesses 124 formed in each of opposed side rails 126a of the base member 126. As can be best seen in FIGS. 8 and 9, and as shown by arrows "C" in FIG. 9, the like size sample containers 130 are received by the previously levelled reference surface 170 as the container positioning member 150 moves downwardly into contact with the base member 126, so as to place the apparatus 120 into its in-use sampling configuration. In the in-use sampling configuration, the container positioning member 150 is positioned over the reference surface 170 with the like size sample containers 130 each positioned within a respective container-receiving socket 160 with the bases 132 of the like size sample containers 130 projecting through the bottom ends 164 of the container-receiving sockets 160, to be supported in weight-bearing relation by the reference surface 170.

In the in-use sampling configuration, (see FIGS. 9 and 11) the like size sample containers 130 are all supported with respect to a substantially level planar surface, namely the reference surface 170. Accordingly, testing errors induced by having the sampling cups supported by an uneven or non-level supporting surface, such as a prior art sample tray, is virtually eliminated. As can be best seen in FIG. 12, the ultrasonic measuring device 117 can take an accurate and meaningful measurement of the height of the top surface of the sample liquid 122 with reference to a substantially level base reference point in each of the like size sample containers 130, and thereby use this data to accurately calculate the volume of the sample liquid 122 in each of the like size sample containers 130, and subsequently to calculate the amount of diluent to be added to accurately achieve the desired final volume of the mixture of the sample liquid 122 and the diluent. More specifically, the sampling head 114 is positioned, by means of the X-Y reference frame 127 operating under control of the computer 112, over a selected sample container 130, whereat the ultrasonic measuring device 117 is able to perform a height measurement of the top surface of the sample liquid 122 in the selected sample container 130. In order to accomplish this measurement, the ultrasonic transducer 117t of the ultrasonic measuring device 117 transmits an ultrasonic signal to the top surface of the sample liquid 122 in the selected sample container 130, as indicated by arrow "D" of FIG. 12. The ultrasonic signal is reflected off the top surface of the sample liquid 122, and the reflected signal, as indicated by arrow "E" of FIG. 12, is received by the ultrasonic sensor 117s. Data related to the height of the top surface of the sample liquid 122, as compared to the height of the base 132 of the sample containers 130 supported by the previously levelled reference surface 170, is received by the computer 112. Based upon the standard geometry of the like size sample containers, the computer 112 is able to accurately calculate the volume of diluent that needs to be added to the selected sample container 130 in order to produce an overall volume of liquid of thirty (30) millilitres.

Next, with reference to FIGS. 13 and 15, the necessary quantity of diluent is extracted by the diluent syringe 108 from the diluent reservoir 109, as indicated by arrows "F", with the diluent syringe valve 108a open to the diluent reservoir 109. The diluent syringe valve 108a is then adjusted to be open to the inlet 115d of the outer diluent tube 115a and the diluent syringe 108 is used to add the necessary quantity of diluent to the selected sample container 130, as indicated by arrows "G".

Finally, as can be seen in FIG. 14, an aliquot of more than twenty-one (21) millilitres of sample liquid 122 is drawn into the sampling syringe 106. The sample liquid 122 is then de-gassed in a suitable manner, the explanation of which is beyond the necessary scope of the present disclosure. The sampling syringe 106 is then used to deliver the de-gassed sample to the optical sensor 111 of the automated particle counter 110, in three aliquots of seven (7) millilitres each, as indicated by arrow "H".

The like size sample containers 130 can then be accurately tested by the automated particle counter 110, due to an absence of interference by "soft particles" with the optical sensor 111 of the automated particle counter 110. It has been found that the present invention produces a potential volume error of less than 2%, which is well within the acceptable tolerances allowed under the ASTM-D7647 test method, and which low level of error is unattainable with prior art automated particle counting systems not involving manual pipetting of the liquid samples and diluents used in testing.

This concludes the description of but one exemplary embodiment of the invention. Many modifications and variations are possible in light of the above teaching and will be apparent to those skilled in the art. The scope of the claims should not be limited by the preferred embodiments set forth in the examples, but should be given the broadest interpretation consistent with the description as a whole.

I claim:

1. An apparatus for presenting samples of liquid contained in like size sample containers for automated testing by a particle counting system, said like size sample containers being of the type each having a base, a continuous sidewall having an inner wall surface and an outer wall surface and extending upwardly from said base and terminating at a top end to define an upwardly facing open mouth, and an engagement portion of said outer wall surface wider than said base, the apparatus comprising:

a base member having an upwardly directed planar reference surface mounted on the base member for adjustment of its horizontal level;

a container positioning member having a horizontally extending main body portion with a plurality of substantially vertically disposed container-receiving sockets formed therein, with said container-receiving sockets each being open at a top end and a bottom end, with each container-receiving socket being defined at said top end by a container-receiving rim portion;

wherein, in an in-use sampling configuration of the apparatus, the container positioning member is positioned over the reference surface with said like size sample containers each positioned within a respective container-receiving socket with the base of said sample containers projecting through the bottom ends of said container-receiving sockets to be supported in weight bearing relation by said reference surface; and, wherein, when said apparatus is removed from said in-use sampling configuration by removal of the container positioning member from positioning over the reference surface, each of the like size sample containers moves downwardly from its position in the in-use sampling configuration relative to the container positioning member to be supported by the engagement portion of said outer wall surface contacting the container-receiving rim portion of the respective container-receiving socket in weight bearing relation therewith.

2. The apparatus of claim 1, wherein, when said container positioning member is in said in-use sampling position, said plurality of substantially vertically disposed container-receiving sockets are positioned, shaped and dimensioned such that a gap exists between the engagement portion of said outer wall surface and the container-receiving rim portion of the respective container-receiving socket.

3. The apparatus of claim 2, wherein, in said in-use sampling position of said apparatus, said container positioning member is supported in weight bearing relation by said base member adjacent said reference surface.

4. The apparatus of claim 3, wherein said main body portion comprises an upper plate and a lower plate connected together in secure relation by spacers.

5. The apparatus of claim 4, wherein said upper plate and said lower plate are each substantially planar.

6. The apparatus of claim 5, wherein said upper plate and said lower plate are substantially parallel one to the other.

7. The apparatus of claim 6, wherein each of said substantially vertically disposed container-receiving sockets comprises an upper container-receiving aperture formed in said upper plate and a lower container-receiving aperture formed in said lower plate in axial alignment with said upper container-receiving aperture.

8. The apparatus of claim 7, wherein said reference surface is adjustably mounted on the base member by at least three gimbal mounts.

9. The apparatus of claim 8, wherein said at least three gimbal mounts comprises four gimbal mounts.

10. The apparatus of claim 9, wherein said gimbal mounts are height adjustable.

11. The apparatus of claim 10, further comprising a plurality of feet projecting downwardly from said main body portion, and a corresponding plurality of co-operating foot-locating recesses located on the base member adjacent to said reference surface.

12. The apparatus of claim 11, wherein said reference surface is substantially planar.

13. The apparatus of claim 12, wherein said reference surface is constructed from a sheet of plate glass.

14. The apparatus of claim 13, wherein said reference surface has a height variation of less than 0.025 millimetres (mm).

15. The apparatus of claim 14, wherein said main body portion is made substantially from metal materials.

16. The apparatus of claim 15, wherein said main body portion is made substantially from aluminium-based materials.

17. The apparatus of claim 16, wherein said main body portion is made substantially from stainless steel-based materials.

18. The apparatus of claim 17, wherein said substantially vertically disposed container-receiving sockets are arranged in a rectangular matrix pattern.

19. The apparatus of claim 18, wherein said substantially vertically disposed container-receiving sockets are substantially annular in plan outline.

20. The apparatus of claim 19, wherein said like size sample containers are each frustum shaped.

* * * * *